(12) United States Patent
Alty et al.

(10) Patent No.: US 7,615,668 B2
(45) Date of Patent: Nov. 10, 2009

(54) METHOD FOR PRODUCING 4,4,4-TRIFLUOROBUTANE-2-ONE

(75) Inventors: Adam Alty, Gainesville, FL (US); Frank Waters, High Springs, FL (US); Richard Du Boisson, Gainesville, FL (US); Yokusu Kuriyama, Niiza (JP); Masamichi Maruta, Saitama (JP)

(73) Assignee: Central Glass Co., Ltd., Tokyo (JP)

( * ) Notice: Subject to any disclaimer, the term of this patent is extended or adjusted under 35 U.S.C. 154(b) by 441 days.

(21) Appl. No.: 11/665,559

(22) PCT Filed: Oct. 18, 2004

(86) PCT No.: PCT/JP2004/034428

§ 371 (c)(1),
(2), (4) Date: Apr. 17, 2007

(87) PCT Pub. No.: WO2006/043946

PCT Pub. Date: Apr. 27, 2006

(65) Prior Publication Data

US 2009/0227821 A1    Sep. 10, 2009

(51) Int. Cl.
C07C 45/00 (2006.01)
C07C 19/08 (2006.01)
(52) U.S. Cl. .................. 568/407; 568/408; 570/155; 570/156
(58) Field of Classification Search .................. 568/407, 568/408
See application file for complete search history.

(56) References Cited

U.S. PATENT DOCUMENTS

| 2,480,560 A | 8/1949 | Downing et al. |
| 2,599,631 A | 6/1952 | Harmon |
| 5,608,128 A | 3/1997 | Nakada et al. |

FOREIGN PATENT DOCUMENTS

| JP | 61-52133 B2 | 11/1986 |
| JP | 10-109954 A | 4/1998 |
| JP | 10-130176 A | 5/1998 |
| JP | 11-80791 A | 3/1999 |
| JP | 11-151401 A | 6/1999 |
| JP | 2001-247508 A | 9/2001 |
| JP | 2001-279296 A | 10/2001 |
| WO | WO 2004/096737 A2 | 11/2004 |

OTHER PUBLICATIONS

Allen et al. Alkene Reactivities in Trifluoroacetic Acid. A Comparison of Norbornene and Protoadamantene in Trifluoroacetic Acid and Aqueous Acid. Journal of the American Chemical Society, 1982, 104, pp. 3145-3149.*
Database CA [Online]; Chemical Abstracts Service, Columbus, Ohio, US; Haszeldine, R. N. et al; "Reactions of fluorocarbon radicals. XV. Synthesis and hydration of 1,1,1-trifluoro-2-butyne"; XP002458448; retrieved from SIN; Database accession No. 1965:19659; abstract & Journal of the Chemical Society 1261-4; Coden: JCSOA9; ISSN: 0368-1769, 1954.
Database Crossfire Beilstein; Beilstein Institut Zur Foerderung Der Chemischen Wissenschaften, Frankfurt Am Main, DE; XPO02458449; Database accession No. 1908573; abstract & J. Am. Chem. Soc., vol. 104, No. 11, 1982, pp. 3145-3149.
Supplementary European Search Report dated Nov. 23, 2007 of EP 04795571.
Tomoya Kitazume et al.; "Synthesis of fluoromenthylated materials in ionic liquids"; Journal of Fluorine Chemistry, 115 (2002) pp. 49-53.
Ling Xiao et al.; "Synthesis of some fluorinated acids, ketones and alcohol derived from 3,3,3-trifluoropropionic acid"; Journal of Fluorine Chemistry, 86 (1997) pp. 99-104.
Tomoya Kizatume et al.; "Study on the effect of di and trifluoromenthyl groups on the Baeyer-Villiger reaction"; Journal of Fluorine Chemistry 80 (1996) pp. 157-158.
Kouichi Murata et al., Asymmetric Synthesis of Both Enantiomers of Acyloxy Methyl 3,3-Difluorolactate; Tetrahedron: Asymmetry vol. 4, No. 5, pp. 889-892, 1993.
Takashi Tsukamoto et al.; Enzymic Optical Resolution of $\alpha,\alpha$-Difluoro-$\beta$-hydroxyketones; Synthetic Communications, 20(20), pp. 3181-3185 (1990).
Takashi Yamazaki et al.; "A Highly Stereocontrolled Synthesis of $\alpha$-Hydroxycyclopropanes Possessing A Trifluoromethyl Group"; Tetrahedron: Asymmetry vol. 1, No. 6, pp. 351-354, 1990.
Tomoya Kizatume et al.; "A Stereoselective Darzen Condensation For The Preparation Of Fluorinated 2.3-Expoxyesters and 2, 3-Epoxyketones"; Chemistry Express, vol. 4, No. 2, pp. 81-84 (1989).
Tomoya Kitazume et al.; "The Synthesis of Optically Active Building Blocks Carrying a Monofluoromethyl Group"; Journal of Fluorine Chemistry, 35 (1987) pp. 477-488.
Yoshimichi Nakayama et al.; "Synthesis of Useful Building Blocks for Monofluorinated Compounds Derived From Trifluorethene"; Journal of Fluorine Chemistry, 29 (1985) pp. 445-458.
Tomoya Kitazume et al.; "Introduction of Center of Chirality Into Fluorocompounds by Microbial Transformation of 2, 2, 2-Trifluoroethanol"; The Chemical Society of Japan; Chemistry Letters, pp. 1815-1818, 1984.
Norbert Muller; "Electrochemical Synthesis of 4,4,4-Trifluoro-2-butanone"; J. Org. Chem. 1983. 48, pp. 1370.
Bernard R. Langlois et al.; "'Pseudo-Cationic' Trifluoromethylation of Enol Esters with Sodium Trifluoromethanesulfinate". Tetrahedron Letters, vol. 33 No. 10, pp. 1291-1992.
Tsuneyoshi Tominaga et al.; "Synthetic applications of the carbanion generated from 4,4,4-trifluorobutan-2-one"; Journal of Fluorine Chemistry, 125 (2004) pp. 67-71.
J.P. Gillet et al.; "Di- and Trifluorovinyllithium Reagents"; Laboratoire de Chimie des Organo-elements, tour 44, 4 place Jussieu, F-75230 Paris Cedex 05, France, pp. 355-360.
Sophie Martin et al.; "Reactivite Des Fluorovinylsilanes Preparation De Cetones $\alpha$-Fluorees"; Tetrahedron Letters, vol. 27, No. 9, pp. 1027-1030, 1986.
International Search Report of PCT/JP2004/034428, date of mailing Feb. 16, 2005.

* cited by examiner

*Primary Examiner*—Sikarl A Witherspoon
(74) *Attorney, Agent, or Firm*—Westerman, Hattori, Daniels & Adrian, LLP

(57) ABSTRACT

The present invention provides a novel method for preparing 4,4,4-trifluorobutane-2-one by providing a fluorobutene selected from the group consisting of 2,4,4,4-tetrafluoro-1-butene, (E)-1,1,1,3-tetrafluoro-2-butene, (Z)-1,1,1,3-tetrafluoro-2-butene, and mixture thereof; and reacting the fluorobutene(s) with a proton acid and water.

17 Claims, No Drawings

METHOD FOR PRODUCING 4,4,4-TRIFLUOROBUTANE-2-ONE

FIELD OF THE INVENTION

The present invention relates to a novel method for producing 4,4,4-trifluorobutane-2-one.

BACKGROUND OF THE INVENTION 4,4,4-Trifluorobutane-2-one is useful as a solvent, detergent and as a versatile building block for pharmaceutical products. International Patent Publication No. 2002-03959 discloses 4,4,4-trifluorobutane-2-one as an ingredient of aerosol pharmaceutical products. Also, 4,4,4-trifluorobutane-2-one is disclosed in Journal of Fluorine Chemistry (1987), 36, 163-170, as an intermediate product for optically-active amino acid derivatives. It is expected to be used in various other fields.

The Journal of Organic Chemistry (1983), 48(8), P. 1370, discloses a method for producing 4,4,4-trifluorobutane-2-one by electrolysis of a mixture of sodium trifluoro acetate and isopropenylacetate in aqueous acetone. This method needs a complicated apparatus for carrying out the electrolysis process. Tetrahedron Letters (1992), 33(10), P.1291, discloses a method for producing 4,4,4-trifluorobutane-2-one by reacting an enol ester represented by $CH_2=C(OAc)CH_3$ or $CH_2=C(OCOCH_3)CH_3$, with sodium trifluoromethanesulfonate and t-butyl hydroperoxide in the presence of a Cu(II) catalyst. Japanese Non-examined Patent Publication No. 10-109954 discloses that a fluorine containing ketone, as represented by $C_nH_mF_{2n+1-m}COCH_3$ where "n" represents an integer number of 2 to 4, and "m" represents 0 or 1, can be prepared by reacting a fluoroalkyl carboxylic acid of $C_nH_mF_{2n+1-m}COOH$ with methyl magnesium bromide in an ether solvent.

These conventional methods may be suitable for laboratory scale synthesis of 4,4,4-trifluorobutane-2-one, but are not easily scaled up for large and industrial manufacture.

It is also known that fluoroolefins subjected to acid hydrolysis may form a fluorine containing ketone (Synthesis, (5), 1986, p. 355, Tetrahedron Letters (1986), 27(9), 1027-1030). However, a fluoroolefin having a structure of C=CF is not always converted into a ketone, as disclosed by Tetrahedron Letters (1986), 27(9), 1027-1030. In this respect, the inventors of the present invention have also confirmed that even if fluoroolefins are contacted with water in the presence of a proton acid, the fluoroolefins do not always proceed with an expected reaction.

On the other hand, Alty et al. invented novel fluorobutene derivatives and a novel method for producing such compounds. The invention of Alty et al. was filed as an International Application No. PCT/US2004/013029, which was assigned to the same assignee of the present invention, and which is incorporated by reference herein. Prior to the invention of Alty et al., it was known that halogenated alkanes subjected to thermal dehydrofluorination affords olefins, but that such thermal dehydrofluorination processes are not practical, especially on an industrial scale because of a low conversion rate and a poor selectivity.

Since the carbon-fluorine bond is very strong, the energy for cleaving the carbon-fluorine is very close to that necessary for cleaving a carbon-carbon bond. In general, the temperature necessary for releasing hydrogen fluoride (HF) from a fluorine compound is far higher than that necessary for releasing hydrogen chloride (HCl) from an analogous chlorinated compound containing a chlorine atom at the same site instead of a fluorine atom. Such a high temperature for the dehydrofluorination causes decomposition and rearrangement, thereby reducing the selectivity of the objective synthesis.

U.S. Pat. No. 2,480,560 discloses that a dehydrofluorination process of five distinct hydrofluorocarbons in the absence of a catalyst gives fluoroolefins at a low selectivity.

On the other hand, it is known that a catalyst can reduce the temperature of the dehydrofluorination, and is expected to improve the selectivity and to avoid decomposition and rearrangement. U.S. Pat. No. 2,599,631 describes a method for producing vinyl fluorides by dehydrofluorination of 1,1-difluoroethane either in a thermal process (no catalyst), or in a catalytic process, and discloses that the catalytic process is more useful. However, a catalyst is easily deactivated after a short time by products formed during the dehydrofluorination process.

It is also known that dehydrofluorination of a fluorine-containing substrate with base can afford fluoroolefins. However, dehydrofluorination processes using base generally give isomers that are different from products obtained by a thermal dehydrofluorination process, and therefore it may be difficult to efficiently produce desired fluoroolefins.

SUMMARY OF THE INVENTION

The present invention provides a method for producing 4,4,4-trifluorobutane-2-one, which is preferable in an industrial production scale. In the present invention, 1,1,1,3,3-pentafluorobutane ($CF_3CH_2CF_2CH_3$; HFC-365mfc) is used as a starting material, which in the first step is subjected to a "dehydrofluorination process," to form a fluorobutene selected from the group consisting of 2,4,4,4-tetrafluoro-1-butene, (E)-1,1,1,3-tetrafluoro-2-butene, (Z)-1,1,1,3-tetrafluoro-2-butene and a mixture thereof. The fluorobutene is subjected to a second step, that is, a reaction with a proton acid and water, so as to produce 4,4,4-trifluorobutane-2-one. The starting material, 1,1,1,3,3-pentafluorobutane, is commercially available, and used for detergents, and foaming agents for e.g., polyurethane, and as a solvent.

The first and/or second steps of the present invention proceed smoothly on a mass production scale, and are not accompanied by any by-products which are difficult to separate. Hence, the method of the present invention is efficient and useful in producing 4,4,4-trifluorobutane-2-one at a high purity.

The steps of the present invention are summarized as follows:

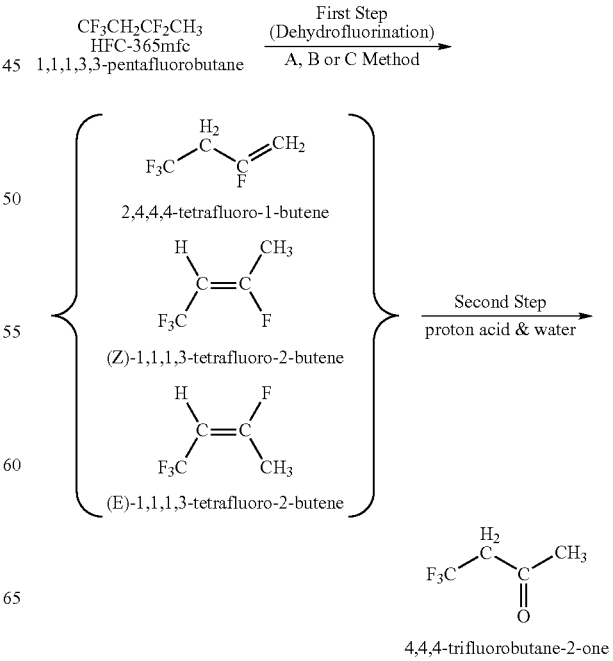

DETAILED DESCRIPTION OF THE INVENTION

The First Step

In a first step, a fluorobutene selected from the group consisting of 2,4,4,4-tetrafluoro-1-butene, (E)-1,1,1,3-tetrafluoro-2-butene, (Z)-1,1,1,3-tetrafluoro-2-butene and mixture thereof is prepared. The fluorobutene of the present invention can be prepared from 1,1,1,3,3-pentafluorobutane as a starting material. 1,1,1,3,3-pentafluorobutane is commercially available as HFC-365mfc. 1,1,1,3,3-pentafluorobutane can be dehydrofluorinated by means of any of the following methods: (1) Method A, (2) Method B and (3) Method C.

(1) Method A

Method A is a process in which the starting material is heated in the absence of a catalyst and a base. The starting material, that is, 1,1,1,3,3-pentafluorobutane, is heated at a temperature of about 200° C. to about 700° C., and in particular, at a temperature of 300° C. to 600° C., and in more particular, at a temperature of 400° C. to 550° C. The range of the temperature, as mentioned here, is preferable for obtaining the optimum conversion rate and selectivity.

As explained above, Method A is carried out in the absence of a base, and therefore, performed under acidic or neutral conditions. In the absence of a base, it is advantageously possible to obtain 2,4,4,4-tetrafluoro-1-butene at a high selectivity.

Method A can be performed either in a flow (continuous) type or in a batch type reaction. In general, preferable selectivity can be obtained by subjecting 1,1,1,3,3-pentafluorobutane to a high temperature for a short time. Also, in general, it is necessary to run the batch type process under autogenous pressure, whereas processes can be run at atmospheric or sub-atmospheric pressure. Thus, the flow type is advantageously used.

In case of the batch type process, 1,1,1,3,3-pentafluorobutane is introduced into a reactor resistant to pressurization and hydrogen fluoride. The reactor is sealed and heated with stirring, and the reaction progress was monitored by, for example, gas chromatographic analysis, until the starting material has been consumed.

In case of the flow type process, 1,1,1,3,3-pentafluorobutane in a gas state is passed through a thermal reaction tube. The thermal reaction tube is made of a material resistant to hydrogen fluoride at a high temperature. In general, the thermal reaction tube is filled with a filler, which is also resistant to hydrogen fluoride, for the purpose of improving the contact. A nickel alloy is preferably used as the reaction tube, and Monel Pro-pack is preferably used as the filler.

In the flow type process, the starting material is heated for a contact time, that is, a "raw material input standard contact time." The contact time is defined as A/B, where "A" represents a "column volume," that is, a value obtained by subtracting the volume of the solid phase occupied by the filler from the inside volume of the reaction tube, and "B" represents a volume of the starting material in a gas state introduced into the reaction tube per second. The value of B is calculated from the molar number of the starting material introduced per second, pressure and temperature, assuming that the gas of the starting material behaves as an ideal gas. In the reaction tube, HF and other gases are generated as by-products, and the molar number is changed, which is, however, not taken into consideration upon the calculation of the "contact time". If the conversion rate is 100%, if the selectivity of the released HF is 100%, and if the released HF behaves as an ideal gas, the contact time would be half, compared with that herein referred to.

According to the present invention, the contact time is not particularly limited. In a case where the reaction temperature is kept at a temperature of 400° C. to 550° C., it is preferable that the starting material is charged at a column volume of about 60 to about 300 column volume per hour, and at a contact time of about 12 seconds to 60 seconds. In particular, the starting material is charged at a column volume of about 90 to about 200 column volume per hour, and at a contact time of about 18 seconds to 40 seconds. It is not preferable to exceed a contact time of 200 seconds because side reactions reduce selectivity and yield. Also it is preferable not to reduce the contact time to less than 1 second because of reduction in the conversion rate.

In view of the above, it is considered optimal, in Method A, that in the absence of a base, 1,1,1,3,3-pentafluorobutane is passed through a reaction tube heated at 400° C. to 550° C. with a contact time of from 18 seconds to 40 seconds.

The optimum contact time is determined based on various conditions including the temperature, shape and filler of the reaction tube. Therefore, depending on such conditions, a rate for delivering the starting material or the contact time should be optimized. Referring to the description of the specification, a person skilled in the art can optimize the conditions of the present invention. In view of collecting and reusing the unreacted starting material, a contact time should be determined, in order to give a conversion rate of 25% or more, and in particular, of 70% or more.

The pressure for the reaction can be set to be lower than, the same as, or higher than, the atmospheric pressure. It is, however, preferable that the reaction is performed under the atmospheric pressure. Also, the reaction vessel may include any inert gas, such as nitrogen and argon, and/or excess HF.

The dehydrofluorination process of the invention can be performed in a gas phase using a well-known chemical engineering apparatus. The units including the reaction tube, and introduction and outflow paths for the reaction materials, are made of a material resistant to hydrogen fluoride. The material for the units includes a stainless steel material such as austenite-type, or a high nickel including alloy and a copper clad steel such as Monel nickel-copper alloy, Hastelloy nickel alloy and Inconel nickel-chromium alloy, which does not limit the present invention.

The reaction mixture obtained by Method A generally includes 2,4,4,4-tetrafluoro-1-butene, as objective, coexisting with (E)-1,1,1,3-tetrafluoro-2-butene and (Z)-1,1,1,3-tetrafluoro-2-butene. Also, 1,1,1,3,3-pentafluorobutane is included as an unreacted staring material.

(2) Method B

Method B is a process in which the starting material, that is, 1,1,1,3,3-pentafluorobutane, is contacted with a base for dehydrofluorination. Method B is generally carried out at a temperature of from about 0° C. to about 300° C.

Method B is advantageous to give (E)-1,1,1,3-tetrafluoro-2-butene and (Z)-1,1,1,3-tetrafluoro-2-butene.

The base, which can be used in Method B, includes: alkali metal hydroxides such as potassium hydroxide, sodium hydroxide, lithium hydroxide and the like; alkali metal carbonates such as sodium carbonate, potassium carbonate, sodium hydrogen carbonate, potassium hydrogen carbonate and the like; alkali earth metal hydroxides such as calcium hydroxide, magnesium hydroxide and the like; and organic bases. The organic basis includes, but is not limited to: tertiary amines such as triethylamine, tributylamine, and trimethylamine; primary amines such as monoethylamine, monobutylamine, cyclohexylamine, and aniline; secondary amines such as diethylamine and dibutylamine; aromatic bases such as pyridine, picoline, lutidine, and ethylpyridine; and strong bases such as guanidine and 1,8-diazabicyclo[5.4.0]dec-7-ene (DBU); and other strong bases such as sodium methoxide, sodium ethoxide, potassium methoxide, and potassium ethoxide. Among them, potassium hydroxide, sodium hydroxide and calcium hydroxide are preferably used, in view of cost.

Method B is accomplished by gradually mixing 1,1,1,3,3-pentafluorobutane with a base. In order to keep a moderate reaction, 1,1,1,3,3-pentafluorobutane is added to a stirred solution of base. Also, it is possible, on the contrary, to add the solution of base to the 1,1,1,3,3-pentafluorobutane.

The base can be used alone or in an aqueous solution, and it is possible to add a phase transfer catalyst. For example, since 85% potassium hydroxide is melted at a temperature of 100° C. or higher, it is convenient that 1,1,1,3,3-pentafluorobutane is dropped into the melted potassium hydroxide with stirring.

The base can be used as a solution. The solvent, which can be used in the present invention, includes, but is not limited to: water; ethers such as diethyl ether, dibutyl ether, methyl butyl ether, phenetol, dioxane, tetrahydrofuran, tetrahydropyran, anisole, benzyl ether, glymes including, e.g., monoglyme, diglyme, and triglyme; and halogen-containing solvents such as methylene chloride, 1,1-dichloroethane, 1,2-dichloroethane, chloroform, carbon tetrachloride, chlorobenzene, and 1,4-bis(trifluoromethyl)benzene. In some cases, a phase-transfer catalyst can be used, which is commonly used, including 18-crown-6, dibenzo-18-crown-6, dicyclohexano-18-crown-6, 12-crown-4, 15-crown-5, dibenzo-24-crown-8, tetraethylammonium chloride, tetraethylammonium bromide, tetrabutylammonium chloride, tetrabutylammonium bromide, ethyltributylammonium bromide, tetraphenylammonium bromide, and tetraphenylphosphonium bromide.

The Method B is not limited to any particular temperature for the reaction, but in order to obtain (E)-1,1,1,3-tetrafluoro-2-butene and (Z)-1,1,1,3-tetrafluoro-2-butene at a high selectivity, it should be carried out at a temperature of 0° C. to 300° C., and in particular, at a temperature of 30° C. to 250° C.

Method B can be carried out at any pressure, but for convenience, Method B is carried out at atmospheric pressure.

The period for the reaction time is not limited, but heating promotes the reaction rate, and the expected reaction is caused immediately upon mixing the starting material with a base. Therefore, as hereinafter shown in Example 2, Method B can be easily carried out in a condition where the starting material is mixed with a base under atmospheric pressure, followed by cooling and collecting a reaction mixture.

Method B can also be performed in a batch manner or in a continuous reaction apparatus, by known chemical engineering techniques. The apparatus used in Method B should be made of a material resistant to a base. The materials, which can be used in the apparatus, includes stainless steels, carbon steels, high nickel containing alloys such as Monel-nickel copper alloy, Hastelloy-nickel alloy and Inconel nickel-chromium alloy, and copper clad steels. In some cases, glass or glass-lined steel can be used.

By-products may be formed in Method B, including fluorine-containing butadiene and butyne, which have relatively low boiling points, so they are easily removed.

(3) Method C

Method C is a process in which the starting material, that is, 1,1,1,3,3-pentafluorobutane, is contacted with a catalyst for dehydrofluorination. The catalyst, which can be used in Method C, includes: (a) an active metal species, (b) a material that is commonly known as a catalyst carrier having a large specific surface area, which is hereinafter referred to as a catalyst carrier, and (c) a carried catalyst, that is, the active metal species carried on the catalyst carrier. These catalysts (a), (b) and (c) generally serve to reduce an activation energy, resulting in converting the starting material into the objectives efficiently, even at a relatively low temperature.

The active metal species (a) includes: titanium, chromium, manganese, iron, cobalt, nickel, copper, zirconium, niobium, molybdenum, ruthenium, rhodium, palladium, silver, hafnium, tantalum, tungsten, rhenium, iridium, platinum, and antimony. Among them, titanium, chromium, manganese, iron, cobalt, nickel, zirconium, niobium, molybdenum, tantalum, and tungsten are preferably used.

The catalyst carrier (b) includes: activated carbons, which are produced by heating vegetable components such as coconut husk, or high boiling point components of petroleum; and oxides such as alumina, titania, niobia, and zirconia. Among them, coconut husk activated carbon is preferably used because it has a large specific surface area. In particular, a catalyst is preferably designed to have a specific surface area of 500-2,000 $m^2/g$.

The active metal species (a) and the catalyst carrier (b) can be used alone, since these substances per se have a catalytic activity. However, the carried catalyst (c), which is a combination of the substances (a) and (b), is preferably used in view of relatively moderate reaction. The carried catalyst (c), which can be preferably used in Method C, includes a catalyst of titanium, chromium, manganese, iron, cobalt, nickel, zirconium, niobium, molybdenum, tantalum, and/or tungsten carried on an activated carbon carrier. Among them, Cr/C (representing chromium atoms carried on an activated carbon), Ti/C, Fe/C, Ni/C, Nb/C and Ta/C are preferable.

In case of using the carried catalyst (c), the active metal species is preferably included in an amount of 1 g to 20 g based on the weight of the metal atom, per 100 g of the activated carbon carrying the active metal species. Within the range of the amount, a high catalytic activity can be expected.

A pretreatment, in which the catalyst is subjected to a flow of a halogenated hydrogen gas such as hydrochloric acid and hydrofluoric acid, can improve the activity and lifetime of the catalyst. It is preferable to carry out the pretreatment by gradually raising the temperature from about 50° C. to a temperature about 50° C. higher than the reaction temperature. Since an adsorption heat is generated immediately after the treatment, it is preferable to dilute the halogenated hydrogen gas with an inert gas such as nitrogen gas, in carrying out the pretreatment. While the pretreatment time is not particularly limited, it is preferably continued for a period of 3 hours to 24 hours.

Depending on the kind of the catalyst, the selectivity of the reaction is varied.

Method C can be performed in a continuous manner or in a batch process. The continuous manner is more convenient.

In case of the batch process, 1,1,1,3,3-pentafluorobutane is introduced into a reactor made of a pressure-proof material, which is also resistant to hydrogen fluoride, following by sealing, stirring and heating. Method C can be terminated after confirming that the starting material is sufficiently consumed, by monitoring the progress of the reaction.

In case of the continuous operation, 1,1,1,3,3-pentafluorobutane is heated and vaporized prior to passage through a reaction tube filled with a catalyst. The continuous operation can be carried out either by means of a fixed catalyst bed or by means of a fluidized catalyst bed. The dehydrofluorination of the present invention can be carried out in a gas phase by using a known chemical engineering apparatus, which is generally made of a material resistant to hydrogen fluoride. The material of the apparatus includes: stainless steel materials such austenite, high nickel containing alloys, and copper cladding steels such as Monel nickel-copper alloy, Hastelloy nickel alloy, and Inconel nickel-chromium alloy.

In the case of the continuous operation, the contact time is preferably set to be 2 seconds to 120 seconds, and in particular, to be 5 seconds to 45 seconds.

The reaction pressure is not limited, but the reaction is preferably carried out at atmospheric pressure. Furthermore, the reaction may be carried out in the presence of an inert gas such as nitrogen and argon, or excess HF.

Compared with Method A, Method C generally proceeds with the expected reaction under milder conditions, thereby affording the target products in a higher yield. Method C can be carried out at a temperature of 150° C. to 700° C., and in particular, of 150° C. to 500° C.

The catalyst used in Method C is high in durability, but when the catalytic activity is reduced, it can be reactivated by using the similar apparatus for the continuous process. Namely, the used catalyst is charged into a reaction tube, and then, a halogenated hydrogen gas such as hydrogen chloride gas and hydrofluoric acid, or a halogen gas such as chlorine gas is passed though instead of 1,1,1,3,3-pentafluorobutane, so as to reactivate the catalyst.

The inventors of the present invention found that the reaction products of the first step have sufficiently distinct boiling points, and that an azeotropic state is not generated. Namely, 2,4,4,4-tetrafluoro-1-butene has a boiling point of 29-30° C.; 1,1,1,3,3-pentafluorobutane has a boiling point of 40° C.; (E)-1,1,1,3-tetrafluoro-2-butene has a boiling point of 18-19° C.; and (Z)-1,1,1,3-tetrafluoro-2-butene has a boiling point of 48-49° C., at the atmospheric pressure. Therefore, an objective component can be isolated at a high purity by means of a distillation process, e.g., under the atmosphere pressure. Also, the unreacted starting material, when collected, can be returned into the reactor for reuse.

However, the fluorobutenes in the mixture are subjected to the second step of the present invention, to be changed into 4,4,4-trifluorobutane-2-one. Therefore, the resultant mixture of the first step can be continuously transferred to the second step of the present invention.

The Second Step

In a second step of the present invention, 4,4,4-trifluorobutane-2-one is prepared from the fluorobutene such as 2,4,4,4-tetrafluoro-1-butene, (E)-1,1,1,3-tetrafluoro-2-butene, (Z)-1,1,1,3-tetrafluoro-2-butene, and mixture thereof. From one aspect of the present invention, the second step of the present invention is carried out after the first step of the present invention, in which 2,4,4,4-tetrafluoro-1-butene, (E)-1,1,1,3-tetrafluoro-2-butene, (Z)-1,1,1,3-tetrafluoro-2-butene and mixture thereof can be obtained. Alternatively, the second step of the present invention can be carried out by using a fluorobutene which is provided, prepared or obtained in a different way from the first step.

In the second step, the fluorobutene are contacted with a proton acid and water, with stirring.

The proton acid which is used in the second step is generally known as a strong acid, including: sulfuric acid; fuming sulfuric acid; hydrogen chloride; hydrogen bromide; hydrogen iodide; nitric acid; alkanesulfonic acids having a carbon number of 1 to 6 such as methanesulfonic acid and ethanesulfonic acid; partially fluorinated alkane-sulfonic acids represented by $C_nH_aF_{2n+1-a}SO_3H$, where "n" represents an integer of 1 to 6, and "a" represents an integer of 1 or more but 2n or less; perfluoro alkanesulfonic acids having a carbon number of 1 to 6 such as trifluoromethanesulfonic acid and pentafluoroethanesulfonic acid; anhydrides of the aforementioned alkanesulfonic acids, partially fluorinated alkanesulfonic acids, and perfluoro alkanesulfonic acids.

In the second step, water is necessary in completing the reaction. The proton acid is often obtained in a state of an aqueous solution, which may be mixed with the fluorobutene.

Without intention to restrict the present invention, the inventors of the present invention consider the mechanism of the second step as follows: First, a proton acid is reacted with the fluorobutene to form an intermediated product of an acid adduct, which is then reacted with water to form 4,4,4-trifluorobutane-2-one. The formation of the acid adduct is generally considered to be a rate determining process, which is generally promoted by raising a concentration of a proton acid. The present invention can be carried out in the following processes, which may improve the yield of the product:

(1) Process A, that is, a process for reacting a fluorobutene with a proton acid, where the proton acid is in a state of a high concentration, is carried out to form an intermediate product of an acid adduct, and then, (2) Process B, that is, a process for adding water to the system including the intermediated product is carried out to continuously complete the second step of the present invention.

In view of the above, it is preferable to use sulfuric acid or perfluoroalkanesulfonic acid such as trifluoromethanesulfonic acid because they are available in a high concentration. It is preferable to use an aqueous solution including a proton acid at a concentration of 60 to 100 wt %, and in particular, of 80 to 100 wt %, and more in particular, of 90 to 100 wt %. Such a proton acid having a high concentration can be mixed with a fluorobutene to form 4,4,4-trifluorobutane-2-one. If the intermediated product remains, water should be supplemented.

In case of using sulfuric acid, it is preferable to use a commercial available product having a concentration of 95 wt % or more, in particular, of 98 wt %.

In case of using a proton acid having a concentration of 10 wt % or less, the reaction may slowly proceed.

The amount of the proton acid mixed with the fluorobutene is not limited, but the proton acid is generally mixed with the fluorobutene at an amount of 0.5 to 10 moles, and in particular, of 0.9 to 5 moles, and more in particular, of 1 to 2 moles, per 1 mole of the fluorobutene. In case of using a sulfuric acid, it is generally mixed with the fluorobutene at an amount of 0.5 to 10 moles, and in order to improve the yield, it is generally mixed with the fluorobutene at an amount of 0.9 to 5 moles, and in particular, of 1 to 2 moles, per 1 mole of the fluorobutene. When the amount of the proton acid is too little, the reaction rate generally becomes slow, resulting in reducing the yield of the product. On the other hand, the amount of the proton acid does not have any upper limit, but in view of improving productivity, it is unnecessary to add too much proton acid.

The amount of water used in the second step is not limited. In the second step, water is theoretically reacted with the fluorobutene at an equivalent ratio. Therefore, water is generally added at an amount of 1 mole or more, per 1 mole of the fluorobutene. If the second step is carried out by way of Processes A and B, as explained above, the total amount of water in the Processes A and B should be 1 mole or more, per 1 mole of the fluorobutene. Although the amount of water does not have any upper limit, it is unnecessary to add too much water, in view of improving productivity. Water is preferably mixed with the fluorobutene at an amount of 0.8 to 10 moles, and in particular, of 1 to 5 moles, and more in particular, of 1 to 2 moles, per 1 mole of the fluorobutene.

If the second step is carried out by way of Processes A and B, as explained above, the Process A can be carried out in a condition where water is included in a reaction vessel at a molar number less than that of the fluorobutene in order to form an acid adduct efficiently, and then Process B can be continuously carried out by adding water such that the total molar number of water added in the reaction vessel becomes more than the molar number of the fluorobutene. As a result, the rate determining process, that is Process A, can be promoted.

The temperature to carry out the second step is not limited. The reaction rate to form the intermediate product depends on the concentration of the proton acid. When using sulfuric acid having a concentration of 95 wt % or more, and in particular, of 98 wt %, a room temperature is generally sufficient to carry out the second step.

Higher water content may reduce a reaction rate, but raising temperature compensates to promote the reaction rate. As shown in the Examples below, the second step can be carried out at a temperature of 60 to 100° C. in case of using an aqueous solution of sulfuric acid at a concentration of 80 wt % and water at a concentration of 20 wt %. If using an aqueous solution of a proton acid at a lower concentration and water at a higher concentration, the temperature for the reaction should be raised in order to maintain an appropriate reaction rate.

It should be noted that the fluorobutene used in the present invention has a boiling point of 18 to 49° C. If the second step is carried out at a temperature much higher than the boiling temperature, the second step should be preferably carried out in a closed reaction vessel such as an autoclave in order to avoid the loss of the materials. In the closed reaction vessel, the pressure is raised due to the autogenous pressure of the reactants. On the other hand, it is possible that the second step can be carried out at atmospheric pressure without using a closed reaction vessel. If the temperature is set to be as high as, or slightly higher than, the boiling point of the reactant butene, such as a temperature of 20 to 40° C., then, the loss of starting materials can be avoided by using a reflux condenser.

The intermediate product can generally be reacted with water rapidly, even at a temperature less than room temperature. If the second step is carried out by way of Processes A and B, as explained above, the Process B is preferably carried out in a reaction vessel in slurry of ice and water, because heat is generated by hydration of the proton acid.

According to the present invention, any solvent other than water, such as aqueous and non-aqueous solvents, can be added, as long as it is stable under the condition of the present invention.

The reaction rate of the second step depends on the conditions including the kind of the fluorobutene, the concentration of the proton acid and the reaction temperature. For example, where concentrated sulfuric acid ($\geq$95 wt %) is added to a molar equivalent of 2,4,4,4-tetrafluoro-1-butene without adding water and at a temperature of 20 to 40° C. with stirring, a homogeneous liquid will be formed during a period of 5 minutes to 1 hour. Stirring is preferably continued for about an hour, to age the resultant liquid. Then, a slurry of ice and water is added to immediately hydrolyze the reaction intermediates to give a solution containing 4,4,4-trifluorobutane-2-one, as objective.

Alternatively, where a solution of sulfuric acid (80 wt %) and water (20 wt %) is used at a temperature of 60 to 100° C., the reaction rate may be reduced. In general, the reaction is preferably continued for a period of 10 to 20 hours. In this case, there is sufficient water, so that an intermediate product of an acid adduct, when formed, is immediately reacted with water to afford 4,4,4-trifluorobutane-2-one, as objective.

In the second step, the extent of reaction can easily be monitored by determining the ratio of the fluorobutene and 4,4,4-trifluorobutane-2-one; It is preferable to continuously monitor the conversion rate.

The material of construction of reaction vessel for the second step is not particularly limited, but the second step uses a strong acid such as sulfuric acid, and generates hydrogen fluoride (HF), so that the material of construction of the reaction vessel should preferably be resistant to such components. In general, it is preferable to use a reaction vessel of a metal or glass, which also has a coating of, for example, a PFA resin or tetrafluoroethylene resin.

After the second step, the resultant mixture can be purified in accordance with known methods. For example, 4,4,4-trifluorobutane-2-one can be extracted by a polar solvent, washed with water to remove the proton acid, and then, isolated by fractional distillation. Thus, 4,4,4-trifluorobutane-2-one can be obtained in high purity.

EXAMPLES

The present invention is described hereinafter in more detail based on Examples, but the present invention is not limited by the description of the Examples.

Preparation of Fluorobutenes

Example 1

A nickel reaction tube having a size of ¾ inches (1.905 cm) diameter and 36 inches (91.4 cm) total length (filled with 200 ml of nickel Propack (void ratio=96%) of 0.24 inches (0.61 cm)) was heated at temperatures shown in 1-1 to 1-4 of Table 1. Under the conditions, 1,1,1,3,3-pentafluorobutane was vaporized by a vaporizer and was passed through the reactor at a rate of 70 g/hr. The exit gasses from the reaction tube were then passed through water to remove hydrogen fluoride (HF). Then, the gas stream was dried with calcium sulfate, collected, and analyzed by gas chromatography, which is hereinafter referred to as GC.

The inside volume of the reaction tube used in Example 1 was 261 cm$^3$, and the volume ("column volume") except the solid phase section of the filler was 253 cm$^3$. Thus, the contact time was from 29 seconds (1-4) to 32 seconds (1-1).

The results were shown in Table 1. "GC %" means area % of each component as determined by a Flame Ionization Detector (FID).

TABLE 1

| No. | Temp. ° C. | 365 mfc GC % | $CF_3CH_2CF{=}CH_2$ GC % | (E)-$CF_3CH{=}CFCH_3$ GC % | (Z)-$CF_3CH{=}CFCH_3$ GC % |
| --- | --- | --- | --- | --- | --- |
| 1-1 | 450 | 73.7 | 18.6 | 3.8 | 2.7 |
| 1-2 | 470 | 69.5 | 23.4 | 4.3 | 2.8 |

TABLE 1-continued

| No. | Temp. °C. | 365 mfc GC % | $CF_3CH_2CF=CH_2$ GC % | (E)-$CF_3CH=CFCH_3$ GC % | (Z)-$CF_3CH=CFCH_3$ GC % |
|---|---|---|---|---|---|
| 1-3 | 500 | 63.5 | 29.6 | 4.3 | 1.3 |
| 1-4 | 520 | 36.4 | 56.9 | 3.4 | 1.6 |

The products were identified by mass spectrometry and NMR (1H, 19F and 13C) and isolated at a purity of 97% by distillation at the atmospheric pressure. The data is as follows.

(1) $CF_3CH_2CF=CH_2$ a colorless, transparent liquid, boiling point: 29° C. to 30° C., $^1$H-NMR solvent: $CDCl_3$, standard substance: TMS δ: 4.88 (dd, J=16.2 Hz, 3.5 Hz, 1H), 4.59 (dd, J=47.3 Hz, 3.5 Hz, 1H), 3.01 (dq, J=16.7 Hz, 9.9 Hz, 2H) $^{19}$F-NMR solvent: $CDCl_3$, standard substance: $CFCl_3$ δ: −66.2 (s, 3F), −95.5~−96.5 (m, 1F) $^{13}$C-NMR solvent:$CDCl_3$, standard substance: TMS δ: 156.54 (d, J=254 Hz), 124.54 (q, J=277 Hz), 96.40 (d, J=18.0 Hz), 37.63 (dq, J=32 Hz, 30 Hz) GLC-MS m/z (rel. intensity), 128($M^+$, 75.2), 113 (5.6), 109 (9.2), 95 (7.6), 89 (23.2), 77 (9.6), 75 (3.2), 69 (22.8), 64 (100), 59 (68.8), 51 (13.6), 45 (16.4)

(2) (E)-$CF_3CH=CFCH_3$ a colorless, transparent liquid boiling point: 18° C. to 19° C., $^1$H-NMR solvent: $CDCl_3$, standard substance: TMS δ: 5.44 (dq, J=16.9 Hz, 7.6 Hz, 1H), 2.14 (d, J=18.7 Hz, 3H) $^{19}$F-NMR solvent:$CDCl_3$, standard substance: $CFCl_3$ δ: −57.2 (s, 3F), −79.5 (s, 1F) GLC-MS m/z (rel. intensity), 128($M^+$, 44.0), 113 (70.4), 109 (32.0), 89 (29.2), 78 (12.8), 77 (23.6), 69 (22.4), 64 (22.8), 59 (29.6), 57 (24.4), 51 (18.8), 45 (14.8), 39 (100)

(3) (Z)-$CF_3CH=CFCH_3$ a colorless, transparent liquid boiling point: 48° C. to 49° C., $^1$H-NMR solvent: $CDCl_3$, standard substance: TMS δ: 5.00 (dq, J=32.7 Hz, 7.6 Hz, 1H, 1.99 (d, J=18.7 Hz, 3H) $^{19}$F-NMR solvent:$CDCl_3$, standard substance: $CFCl_3$ δ: −58.9 (dd, J=17.1 Hz, 6.4 Hz, 3F), −83.2~−83.7 (m, 1F) GLC-MS m/z (rel. intensity), 128 ($M^+$, 44.0), 113 (72.0), 109 (37.2), 89 (31.2), 78 (11.6), 77 (25.6), 69 (25.6), 64 (22.4), 59 (29.6), 57 (25.2), 51 (20.0), 45 (15.2), 39 (100)

Example 2

A 250 ml flask was equipped with a magnetic stirrer having a coating of polytetrafluoroethylene, a dropping funnel (under the liquid level), a reflux condenser and a Vigreux column. The outlet of the column was connected via an oil bubbler, to trap cooled to −78° C. 80 g of 85% potassium hydroxide flake was placed in the flask, and heated at a temperature of 210° C. in an oil bath, where upon 1,1,1,3,3-pentafluorobutane was slowly added through the dropping funnel. A mixture of the reaction products and the unreacted starting material were collected in the cold trap. Thereby obtained mixture was found to include seven kinds of substances in addition to the starting material. After completion of the reaction, an analysis of the trapped product mixture by gas chromatography showed that the crude mixture included the starting material at 50%, (E)-$CF_3CH=CFCH_3$ configuration at 17.8%, (Z)-$CF_3CH=CFCH_3$ configuration at 17.8%, $CF_3CH_2CF=CH_2$ at 8.0%, and the remainder including butadiene ($CF_2=CHCF=CH_2$) and butyne ($CF_3C≡CCH_3$) at 6.4%. (E)-$CF_3CH=CFCH_3$ having a boiling point of 18-19° C. and (Z)-$CF_3CH=CFCH_3$ having a boiling point of 48-49° C. were separated by distillation to a purity of 98% or higher. These products were identified by mass spectrometry and NMR spectroscopy.

Examples 3-1 to 3-4

A catalyst pretreatment was carried out as follows: 15 g of a catalyst obtained by Catalyst Preparation Example 1, as described hereinafter, were put into the center portion of a stainless steel reaction tube having an inner diameter of 28.4 mm and an axial length of 400 mm. While nitrogen gas was passed into the reaction tube at a rate of 50 ml/min, the temperature was gradually raised at 500° C. After holding this condition for a period of 5 hours, the heating was terminated, and allowed to cool to a temperature of 50° C. Then, hydrogen chloride gas (HCl) was introduced into the reaction tube such that a flow rate of HCl was initially at 5 ml/min and then gradually raised at 50 ml/min, while the flow rate of nitrogen gas was reduced from 50 ml/min to 10 ml/min. Then, the temperature was raised at 400° C. at a rate of 100° C./hr. This condition was kept for a period of 3 hours, thereby completing the catalyst pretreatment.

Then, 1,1,1,3,3-pentafluorobutane (365mfc), vaporized by a vaporizer, was introduced into the reaction tube at a reaction temperature shown in Table 2 and at a rate to have a contact time as shown in Table 2, while nitrogen gas was also introduced at a rate of 10 ml/min. The flow of nitrogen gas was, however, neglected in the calculation of the contact time. The exit gas from the reaction tube was then passed through water in order to remove hydrogen fluoride (HF), dried with calcium sulfate, collected, and analyzed by gas chromatography. The results are shown in Table 2.

Examples 4-1 to 4-4

Examples 4-1 to 4-4 were carried out in the same manner as Examples 3-1 to 3-4 except that a catalyst obtained by Catalyst Preparation Example 2, as described hereinafter was used instead. The results are shown in Table 2.

Examples 5-1 to 5-2

Examples 5-1 and 5-2 were carried out in the same manner as Examples 3-1 to 3-4 except that a catalyst obtained by Catalyst Preparation Example 3, as described hereinafter, was used instead. The results are shown in Table 2.

Examples 6-1 to 6-4

Examples 6-1 to 6-4 were carried out. First, a catalyst pretreatment was carried out in the same manner as described in Example 3-1 to 3-4 except that 15 g of a catalyst obtained by Catalyst Preparation 2, was used instead. Then, the reaction was started by passing gaseous 1,1,1,3,3-pentafluorobutane into the reaction tube held at a temperature of 250° C. at a rate corresponding to a contact time of 21 seconds. During the reaction, nitrogen gas was also introduced at a rate of 10 ml/min. The flow volume of the nitrogen gas was not considered in calculating the contact time. In Example 6-1, the exit gas at the initial stage of the reaction was analyzed by means of gas chromatography. In Examples 6-1 to 6-4, the exit gas was treated in the same manner as that of Examples 3-1 to 3-4, reaction was continued for a period of 150 hours under the same conditions as above. In Example 6-4, 150 hours after restarting the reaction, the exit gas was analyzed by means of gas chromatography. The results of Examples 6-1 to 6-4 are shown in Table 3.

TABLE 2

| | Catalyst | Reaction Temp (°C.) | RMISCT* (s) | 365 mfc GC % | $CF_3CH_2CF{=}CH_2$ GC % | (E)-$CF_3CH{=}CFCH_3$ GC % | (Z)-$CF_3CH{=}CFCH_3$ GC % | $CF_2{=}C{=}CH_2$ GC % | $CF_2{=}CH{-}CF{=}CH_2$ GC % |
|---|---|---|---|---|---|---|---|---|---|
| Ex. 3-1 | C* | 300 | 30 | 87.3 | 6.8 | 2.2 | 3.7 | 0.0 | 0.0 |
| Ex. 3-2 | C* | 350 | 28 | 48.1 | 29.3 | 10.9 | 9.2 | 0.0 | 2.1 |
| Ex. 3-3 | C* | 400 | 26 | 47.3 | 30.5 | 10.4 | 9.3 | 0.0 | 2.3 |
| Ex. 3-4 | C* | 450 | 24 | 19.5 | 51.8 | 6.5 | 6.1 | 8.9 | 7.3 |
| Ex. 4-1 | Cr/C | 150 | 20 | 91.1 | 4.1 | 1.9 | 3.0 | 0.0 | 0.0 |
| Ex. 4-2 | Cr/C | 200 | 18 | 54.9 | 21.9 | 14.0 | 9.0 | 0.0 | 0.0 |
| Ex. 4-3 | Cr/C | 250 | 16 | 6.3 | 47.1 | 27.9 | 16.0 | 0.0 | 2.5 |
| Ex. 4-4 | Cr/C | 320 | 14 | 9.8 | 46.2 | 20.4 | 12.3 | 0.0 | 10.5 |
| Ex. 5-1 | Ti/C | 210 | 41 | 58.8 | 32.5 | 2.0 | 1.2 | 0.0 | 0.1 |
| Ex. 5-2 | Ti/C | 250 | 38 | 24.2 | 55.3 | 8.3 | 4.8 | 0.0 | 0.4 |

*C: Activated Carbon
*RMISCT: Raw Material Input Standard Contact Time (Contact Time)

TABLE 3

| | 365 mfc GC % | $CF_3CH_2CF{=}CH_2$ GC % | (E)-$CF_3CH{=}CFCH_3$ GC % | (Z)-$CF_3CH{=}CFCH_3$ GC % | $CF_2{=}C{=}CH_2$ GC % | $CF_2{=}CH{-}CF{=}CH_2$ GC % |
|---|---|---|---|---|---|---|
| Ex. 6-1 (immediately after reaction start) | 28.0 | 32.6 | 25.6 | 13.3 | 0.0 | 0.4 |
| Ex. 6-2 (150 hr after reaction start) | 51.7 | 22.2 | 14.4 | 11.4 | 0.0 | 0.3 |
| Ex. 6-3 (immediately after reaction restart) | 24.0 | 33.1 | 27.6 | 11.6 | 0.0 | 0.7 |
| Ex. 6-4 (150 hr after reaction restart) | 31.0 | 29.1 | 25.0 | 14.3 | 0.0 | 0.5 | prior to the gas chromatography. The reaction was continued for a period of 150 hours under the same conditions as above. In Example 6-2, 150 hours after beginning the reaction, an outflow gas was analyzed by means of gas chromatography. The conversion was 72% at the initial stage of the reaction, which slowly reduced to 48% during the reaction period of 150 hours. Catalyst regeneration was carried out, as follows: After the flow of 1,1,1,3,3-pentafluorobutane was stopped, the reactor tube was flushed with nitrogen at 50 ml/min. Then, hydrogen chloride was introduced at a rate of 50 ml/min, and the nitrogen gas flow rate was reduced at 10 m/min. This treatment was maintained for a period of 24 hours to regenerate the catalyst, while the temperature of the catalyst bed was kept at a temperature of 250° C. After the regeneration, hydrogen chloride was stopped. Then, the dehydrofluorination reaction was restarted under the same conditions as before. In Example 6-3, the exit gas obtained immediately after regeneration of the catalyst was analyzed by means of gas chromatography. After the restart of the reaction, the Catalyst Preparation Example 1

500 g of activated carbon (purchased from Sigma-Aldrich Corporation) was dried for 24 hours in an vacuum oven at a temperature of 120° C. under a pressure of 10 Torr (1,330 Pa). Then, the pressure was increased to atmospheric pressure by introducing nitrogen gas, and the catalyst allowed to cool down to room temperature, thereby completing the preparation of an activated carbon catalyst. The obtained catalyst was put into a sealable glass container, which was placed in a dessicator until its use.

Catalyst Preparation Example 2

45.8 g of $Cr(NO_3)_3$ was dissolved in 400 g of deionized water. The resulting solution was gradually added to 100 g of activated carbon (purchased from Sigma-Aldrich Corporation). The mixture was slowly stirred twice, first immediately after the addition and second, at a time 1 hour after the addition, followed by stagnation for a period of 48 hours. Then, water was removed by a rotatory evaporator, followed by drying it for a period of 24 hours in a vacuum oven at a temperature of 150° C. under a pressure of 10 Torr (1,330 Pa), thereby obtaining a Cr/C catalyst. This catalyst was put into a sealable container, and stored in a dessicator until its use.

Catalyst Preparation Example 3

100 g of the activated carbon (obtained in Catalyst Preparation Example 1) was placed in a recrystallization dish. Then, 59.2 g of titanium(IV) isopropoxide [Ti(OCHMe$_2$)$_4$] (purchased from Sigma-Aldrich Corporation) was slowly added with stirring, followed by stagnation for a period of 48 hours. Then, 100 g of deionized water was slowly added by spraying and stirring, followed by drying for a period of 48 hours in a vacuum oven at a temperature of 150° C. under a pressure of 10 Torr (1,330 Pa), thereby obtaining a Ti/C catalyst. This catalyst was put into a sealable container, and stored in a dessicator until its use.

Comparative Example 1

A nickel reaction tube having a size of ¾ inches (1.91 cm) diameter and 36 inches (91.4 cm) total length was heated at a temperature of 630° C., and the reaction tube was filled with a nickel Pro-pack (void ratio=96%) of 0.24 inches (0.61 cm), which improved mixing and heat transfer. 1,1,1,4,4,4-hexafluorobutane was vaporized by the same manner as described in Example 1, and introduced to the reactor tube at a flow rate such that a contact time became 30 seconds. The gas passing through the tube was then scrubbed with water to remove hydrogen fluoride (HF), dried it with calcium sulfate, and then analyzed by gas chromatography.

Gas chromatographic analysis showed the reaction product to contain, the starting material, that is, 1,1,1,4,4,4-hexafluorobutane, 43.2%, and 3,3,3-trifluoropropene 30.6%, and trifluoromethane, 17.1%. However, 1,1,4,4,4-pentafluoro-1-butene was not detected in the resultant mixture.

Comparative Example 2

Using the same apparatus as described in Comparative Example 1, 2-(trifluoromethyl)-1,1,1-trifluoropropane was introduced in a form of gas at a temperature of 660° C. According to the GC analysis of the exit gas contained, the starting material, 18.9%, 3,3,3-trifluoropropene, 24.5%, and trifluoromethane 43.5%. However, 2-trifluoromethyl-1,1-difluoropropene was not detected.

Preparation of 4,4,4-Trifluorobutane-2-one

Example 7

360 g of a concentrated sulfuric acid (3.56 mol, 1.01 eq) and 90 g of water (5.00 mol, 1.42 eq) were placed in a stainless steel reactor, and the inside temperature maintained at 2° C. Then, 451 g of 2,4,4,4-tetrafluoro-1-butene (3.52 mol, 1.00 eq) was added thereinto, and the reaction vessel was sealed and heated in an oil bath held at a temperature of 85° C. to 86° C. The stirred reaction vessel had an internal temperature of 63° C. to 66° C., which was held for a period of 16 hours, followed by cooling to room temperature. The thereby obtained reaction solution was poured into iced water, and the organic layer separated. The collected organic layer was washed with a saline solution, and then, the resultant mixture was subjected to an extraction process twice with methylene chloride at volumes of 200 ml and 50 ml. The thereby collected organic layer was distilled under atmospheric pressure, to obtain 154 g of 4,4,4-trifluorobutane-2-one, as a colorless oil. Gas chromatographic analysis showed that the collected product was 4,4,4-trifluorobutane-2-one at a purity of 99.5%. Since 444 g of the product is theoretically obtained, a yield of Example 7 was 34.5%, based on the purity.

Example 8

A mixture of tetrafluorobutenes containing 13% of (E)-1,3,3,3-tetrafluoro-2-butene, 9% of (Z)-1,3,3,3-tetrafluoro-2-butene, 24% of 2,4,4,4-tetrafluoro-1-butene, in HFC-365mfc (54%) was prepared by gas phase dehydrofluorination of HFC-365mfc. Into a three-neck flask equipped with a reflux condenser was placed, 81 g of a concentrated sulfuric acid (801 mmol, 1.07 eq) and 209.0 g of the crude product (751 mmol of the butanes in total), and the temperature was gradually raised to 38 to 41° C. After 5 minutes, the reaction liquid was homogeneous, and reflux ceased; Stirring was continued for a further 55 minutes. The reaction liquid was poured into 300 g of iced water, followed by extraction with methylene chloride (2×100 ml). The organic layers were combined, washed with 100 ml of a saturated saline solution, and dried with calcium chloride. Gas chromatographic analysis showed a conversion of 99% based on the total of the fluorobutenes contained in the starting material.

The collected organic layer was distilled under atmospheric pressure, to afford 71.4 g of 4,4,4-trifluorobutane-2-one as a colorless oil. Gas chromatographic analysis confirmed that the product was 4,4,4-trifluorobutane-2-one with a purity of 99.7%. Since the theoretical yield is calculated at 94.6 g, Example 8 gave an actual yield of 75.2%, based on the purity.

Example 9

Into a stainless steel reaction vessel was placed 23.9 g of a concentrated sulfuric acid (244 mmol, 1.39 eq) and 6.0 g of water (333 mmol, 1.90 eq). Then, the reaction vessel was sealed and cooled at a temperature of −78° C., and 22.5 g of (E)-1,3,3,3-tetrafluoro-2-butene (176 mmol), was transferred in vacuum, and the reaction mixture stirred for a period of 17 hours at a temperature of 71° C. to 72° C. The reaction vessel was cooled in iced water, and gasses inside the reaction vessel were vented. After the termination of the reaction, the reaction mixture separated into two layers. The organic layer was washed with 50 ml of water and gas chromatographic analysis showed that the organic layer contained 80% of (E)-1,1,1,3-tetrafluoro-2-butene, 6% of (Z)-1,1,1,3-tetrafluoro-2-butene, and 14% of 4,4,4-trifluorobutane-2-one.

Example 10

Into a three-neck flask equipped with a dry ice/methanol cooled reflex condenser was placed 15.0 g of 2,4,4,4-tetrafluoro-1-butene (117 mmol, 1.00 eq) and 7.0 g of silica gel (117 mmol, 1.00 eq). The flask was cooled with iced water and a mixture of 18.3 g of trifluoromethanesulfonic acid (122 mmol, 1.04 eq) and 3.0 g of water (167 mmol, 1.42 eq) was added from a dropping funnel. Then, the flask was warmed to 30° C. to 37° C. for a period of 23.5 hours. After the completion of the reaction, 100 ml of water was added and extracted with methylene chloride(2×100 ml). The combined organic layers were washed with 100 ml of water and dried with magnesium sulfate. Gas chromatographic analysis of the organic layer showed a 63% conversion for 4,4,4-trifluorobutane-2-one.

Example 11

Into a three-neck flask equipped with a dry ice/methanol cooled reflux condenser was placed 15.0 g of 2,4,4,4-tetrafluoro-1-butene (117 mmol, 1.00 eq) and 11.9 g of a concentrated sulfuric acid (119 mmol, 98 wt %), and then, the temperature was raised with stirring. At a temperature of 30° C., reflux started, and the sulfuric acid and 2,4,4,4-tetrafluoro-1-butene mixture become homogenous. After 15 minutes, continuing the stirring, the mixture was cooled in iced water, and then 7.0 g of silica gel (117 mmol, 1.00 eq) was added therein so as to avoid glass corrosion by the HF co-product. Thereafter, 3 g of water (167 mmol) were added, and after removing silica gel by filtration, the temperature was raised to 80° C. The reaction mixture was cooled, poured into 100 g of iced water (2×100 ml), and extracted with methylene chloride (2×100 ml). The combined organic layers were washed with 100 ml of water and dried with magnesium sulfate. Gas chromatographic analysis of the organic layer showed a 92% conversion for 4,4,4-trifluorobutane-2-one.

Comparative Example 3

32.3 g of a concentrated sulfuric acid (329 mmol, 1.10 eq) was placed in a stainless steel reaction vessel. Then, the reaction vessel was sealed and cooled to −78° C., and 34.0 g of 1,3,3,3-tetrafluoropropene (298 mmol) was transferred in vacuo and the mixture by stirred for a period of 17.5 hours at a temperature of 60° C. Then, the reaction vessel was cooled by iced water, showing an inside pressure of 0.35 MPa. The liquid phase in the reaction vessel was collected, diluted washed with water and extracted with methylene chloride. Gas chromatographic analysis, however, showed that no ketones, as objective, were found therein.

Comparative Example 4

15.7 g of a concentrated sulfuric acid (160 mmol, 1.01 eq) was placed in a stainless steel reactor. Then, the reaction vessel was sealed and cooled to −78° C., and 18.0 g of 2,3,3,3-tetrafluoropropene (158 mmol), was transferred in vacuo and the mixture stirred for a period of 4.5 hours at a room temperature, and continuously stirred for a further 16.5 hours at a temperature of 76° C. to 90° C. Then, the reaction vessel was cooled by iced water, showing an inside pressure of 0.30 MPa. The liquid phase in the reaction vessel was collected, and diluted with water, and extracted with methylene chloride. Gas chromatographic analysis, however, showed that no ketones, as objective, were found therein.

Comparative Example 5

14.4 g of a concentrated sulfuric acid (147 mmol, 1.10 eq) was placed in a stainless steel reaction. Then, the reaction vessel was sealed, cooled to −78° C., and 20.0 g of 1,1,2,3,3,3-hexafluoropropane (133 mmol), was transferred in vacuo and the mixture, stirred for a period of 13 hours at a temperature of 60° C., and continuously stirring it for a further period of 2 hours at a temperature of 120° C., and then continuously stirring it for a further period of 3 hours at a temperature of 140° C. Then, the reaction vessel was cooled by iced water. The liquid phase in the reaction vessel was collected, and diluted with water, and extracted with methylene chloride.

Gas chromatographic analysis, however, showed that no ketones, as objective, were found therein.

What is claimed is:

1. A method for preparing 4,4,4-trifluorobutane-2-one, comprising:
    providing a fluorobutene selected from the group consisting of 2,4,4,4-tetrafluoro-1-butene, (E)-1,1,1,3-tetrafluoro-2-butene, (Z)-1,1,1,3-tetrafluoro-2-butene, and a mixture thereof; and
    reacting the fluorobutene with a proton acid and water to form 4,4,4-trifluorobutane-2-one.

2. A method according to claim 1, wherein the proton acid is selected from the group consisting of sulfuric acid, fuming sulfuric acid, hydrogen chloride, hydrogen bromide, hydrogen iodide, nitric acid, alkanesulfonic acids having a carbon number of 1 to 6; partially fluorinated alkanesulfonic acids represented by $C_nH_aF_{2n+1-a}SO_3H$, where "n" represents an integer of 1 to 6, and "a" represents an integer of 1 or more but 2n or less; perfluoroalkane sulfonic acids having a carbon number of 1 to 6; anhydrides of the alkanesulfonic acids, the partially fluorinated alkanesulfonic acids, and the perfluoroalkanesulfonic acids.

3. A method according to claim 1, wherein the proton acid is a concentrated sulfuric acid having a concentration of 95 wt % or more.

4. A method according to claim 1, wherein the proton acid is in a state of an aqueous solution.

5. A method according to claim 1, wherein the proton acid is added at an amount of 0.5 to 10 moles, and water is added at an amount of 0.8 to 10 moles, per a mole of the fluorobutene.

6. A method according to claim 1, wherein the fluorobutane is prepared by subjecting 1,1,1,3,3-pentafluorobutane to a dehydrofluorination process.

7. A method according to claim 6, wherein the dehydrofluorination process is carried out by thermolysis of 1,1,1,3,3-pentafluorobutane at a temperature of 200° C. to 700° C.

8. A method according to claim 6, wherein the dehydrofluorination process is carried out by heating 1,1,1,3,3-pentafluorobutane at a temperature of 0° C. to 300° C., in the presence of a base.

9. A method according to claim 8, wherein the base is selected from the group consisting of alkali metal hydroxides, alkali metal carbonates, alkali earth metal hydroxides, and organic bases.

10. A method according to claim 6, wherein the dehydrofluorination process is carried out by heating 1,1,1,3,3-pentafluorobutane in the presence of a catalyst.

11. A method according to claim 10, wherein the catalyst is selected from the group consisting of an activated carbon, a chromium catalyst carried on an activated carbon (Cr/C), and a titanium catalyst carried on an activated carbon (Ti/C).

12. A method according to claim 6, wherein after the dehydrofluorination process, the crude mixture of fluorobutenes obtained is reacted with the proton acid and water without purification.

13. A method for preparing 4,4,4-trifluorobutane-2-one, comprising:
    providing a fluorobutene selected from the group consisting of 2,4,4,4-tetrafluoro-1-butene, (E)-1,1,1,3-tetrafluoro-2-butene, (Z)-1,1,1,3-tetrafluoro-2-butene, and a mixture thereof;
    first reacting the fluorobutene(s) with a proton acid; and
    second adding water therein to form 4,4,4-trifluorobutane-2-one.

14. A method according to claim 13, wherein the proton acid is selected from the group consisting of sulfuric acid, fuming sulfuric acid, hydrogen chloride, hydrogen bromide, hydrogen iodide, nitric acid, alkanesulfonic acids having a carbon number of 1 to 6; partially fluorinated alkanesulfonic acids represented by $C_nH_aF_{2n+1-a}SO_3H$, where "n" represents an in of 1 to 6, and "a" represents an integer of 1 or more but 2n or less; perfluoro alkanesulfonic acids having a carbon number of 1 to 6; anhydrides of the alkanesulfonic acids, the partially fluorinated alkanesulfonic acids, and the perfluoroalkanesulfonic acids.

15. A method according to claim 13, wherein the proton acid is a concentrated sulfuric acid having a concentration of 95 wt % or more.

16. A method according to claim 13, wherein the proton acid is in a state of an aqueous solution, and wherein the aqueous solution includes water at a molar number less than that of the fluorobutene, and then, water is supplemented such that a total molar number of water included in a reaction vessel exceeds a molar number of the fluorobutene.

17. A method according to claim 13, wherein the proton acid is added at an amount of 0.5 to 10 moles, and water is added at an amount of 0.8 to 10 moles, per a mole of the fluorobutene.

* * * * *